(12) United States Patent
Colberg et al.

(10) Patent No.: US 7,129,350 B2
(45) Date of Patent: Oct. 31, 2006

(54) COUPLING PROCESS AND INTERMEDIATES USEFUL FOR PREPARING CEPHALOSPORINS

(75) Inventors: Juan C. Colberg, Gilford, CT (US); Maurizio Zenoni, Paullo (IT); Giovanni Fogliato, Barzana (IT); Alessandro Donadelli, Casalpusterlengo (IT)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/776,795

(22) Filed: Feb. 11, 2004

(65) Prior Publication Data

US 2004/0167327 A1    Aug. 26, 2004

Related U.S. Application Data

(63) Continuation of application No. 10/006,279, filed on Dec. 4, 2001, now abandoned.

(60) Provisional application No. 60/256,014, filed on Dec. 4, 2000.

(51) Int. Cl.
*C07D 501/20* (2006.01)
*C07D 501/04* (2006.01)
*C07D 405/12* (2006.01)
*C07F 9/6539* (2006.01)

(52) U.S. Cl. .................. 544/222; 540/360; 548/119
(58) Field of Classification Search ................ 544/222
See application file for complete search history.

(56) References Cited

U.S. PATENT DOCUMENTS 6,825,344 B1* 11/2004 Best et al. ................. 540/222
2004/0267008 A1* 12/2004 Colberg et al. ............ 540/222

FOREIGN PATENT DOCUMENTS

WO   WO92/1696 A1 *  2/1992

* cited by examiner

Primary Examiner—Mark L. Berch

(74) *Attorney, Agent, or Firm*—Scully, Scott, Murphy & Presser, P.C.

(57) ABSTRACT

A process for the preparation of 3-cyclic-ether-substituted cephalosporins of formula I

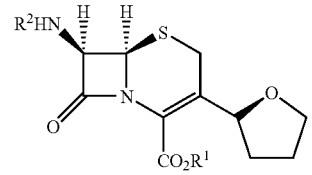

wherein the group $CO_2R^1$ is a carboxylic acid or a carboxylate salt and $R^2$ has the formula:

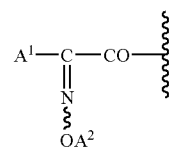

wherein
$A^1$ and $A^2$ have the meanings given in the specification by reacting compound of formula II:

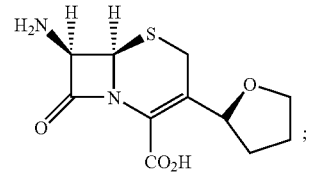

wherein $R^2$ is as defined above and $R^3$ is para-nitrobenzyl or allyl with a compound $R^2$ L wherein $R^2$ is as defined above; and L is di-$(C_{1-6}$ alkyl)phosphorothioate in the presence of a solvent and a base.

12 Claims, No Drawings

COUPLING PROCESS AND INTERMEDIATES USEFUL FOR PREPARING CEPHALOSPORINS

REFERENCE TO RELATED APPLICATIONS

The present application is a continuation of U.S. patent application, Ser. No. 10/006279, filed Dec. 4, 2001, now abandoned, which claims the benefit of U.S. provisional application, Ser. No. 60/256014, filed Dec. 4, 2000.

BACKGROUND OF THE INVENTION

This invention relates to a novel process for the preparation of 3-cyclic-ether-substituted cephalosporins. The invention also relates to novel processes for preparing zwitterions, para-nitrobenzyl esters and allyl esters useful in the preparation of the above cephalosporins. The invention also relates to 3-cyclic-ether-substituted cephalosporins. These compounds possess certain advantageous properties, such as crystalline form and high enantiomeric excess (e.e.).

The 3-cyclic-ether-substituted cephalosporins prepared by the methods of the present invention have prolonged and high levels of antibacterial activity and possess good absorption parentally in humans and animals. The 3-cyclic-ether-substituted cephalosporins prepared by the processes of the present invention contain a cyclic ether substituent at carbon 3 of the cephalosporin nucleus.

GB 1405758 describes alternative methods of preparation of certain 3-cyclic-ether-substituted cephalosporins.

J. Antibiotics (1994), vol. 47(2), page 253, and WO 92/01696 also describe alternative methods of preparation of compounds of formula I, as defined herein below, and compounds useful in said processes.

U.S. Pat. Nos. 6,020,329 and 6,077,952 describe salts, polymorphs, solvates and hydrates of 3-cyclic-ether-substituted cephalosporins.

U.S. Pat. No. 6,001,997 describes alternative methods of preparations of 3-cyclic-ether-substituted cephalosporins.

United States Non-Provisional Patent Application entitled "Process and Ester Derivatives Useful For Preparation of Cephalosporins", filed Dec. 4, 2001, refers to intermediates and processes to prepare 3-cyclic-ether-substituted cephalosporins.

Each of the above referenced publications, patents and patent applications is hereby incorporated by reference in its entirety.

The present inventors have discovered a novel compound of formula I, as defined herein below. The present inventors have also discovered a high-yielding process for the preparation of said compounds of formula I.

SUMMARY OF THE INVENTION

The present invention relates to a process for the preparation of a 3-cyclic-ether-substituted cephalosporin of the formula I

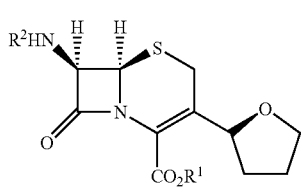

or the pharmaceutically acceptable salts thereof, wherein
the group $CO_2R^1$ is a carboxylic acid or a carboxylate salt; and
$R^2$ has a formula:

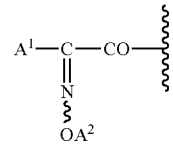

wherein
$A^1$ is $C_{6-10}$aryl, $C_{1-10}$heteroaryl or $C_{1-10}$heterocyclyl;
$A^2$ is hydrogen, $C_{1-6}$alkyl, $C_{3-10}$cycloalkyl, $C_{6-10}$aryl, $C_{1-6}$alkyl(CO)($C_{1-6}$)alkyl-O—, HO(CO)($C_{1-6}$)alkyl, mono-($C_{6-10}$aryl)($C_{1-6}$alkyl), di-($C_{6-10}$aryl)($C_{1-6}$alkyl) or tri-($C_{6-10}$aryl)($C_{1-6}$alkyl);
comprising reacting
a compound of formula II

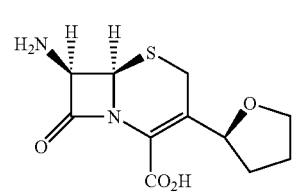

with a compound of the formula III $$R^2L \qquad (III)$$

wherein $R^2$ is as defined above, and L is a leaving group, in the presence of a solvent and a base. Optionally, the aforesaid process may be performed in the presence of a coupling agent and a catalyst.

Preferably, the group $OA^2$ of said compounds of formula III is cis to the amide linkage, i.e., the Z-configuration is preferred.

Suitable solvents for the aforesaid process of conversion of compounds of formula II into compounds of formula I of the invention include water, acetone, tetrahydrofuran, ethyl acetate, dimethylacetamide, dimethylformamide, acetonitrile, methylene chloride, 1,2-dichloroethane or mixtures thereof. In one embodiment of the invention, the solvent is tetrahydrofuran. In another embodiment of the invention, the solvent is ethyl acetate. Preferably, the solvent is water, acetone or mixtures thereof. More preferably the solvent is a mixture of acetone and water. Most preferably the solvent is a 1.3:1 mixture of acetone and water.

Suitable bases for the aforesaid conversion of the invention include diisopropylethylamine or sodium hydroxide. Preferably, the base is sodium hydroxide, most preferably 15% aqueous sodium hydroxide.

Suitable coupling agents for the aforesaid conversion of the invention include N,N'-diethylcarbodiimide, N,N'-dipropyl carbodiimide, N,N'-diisopropylcarbodiimide, N,N'-dicyclohexylcarbodiimide, N-ethyl-N'-[3-(dimethylamino)propyl]carbodiimide, N,N'-carbonyldiimidazole or N,N'-carbonyldithiazole. A preferred coupling agent is N,N'-dicyclohexylcarbodiimide. Preferably, the aforesaid conversion is conducted in the absence of any coupling agents.

Suitable catalysts for the aforesaid conversion of the invention include Lewis acids. Suitable Lewis acids are selected from the group consisting of boron trihalide, such as boron tribromide, and aluminum halide, such as aluminum chloride. Preferably, the aforesaid conversion is conducted in the absence of any catalysts.

The aforesaid conversion of the invention can be conducted at a temperature of about −40° C. to about +30° C., preferably about +20° C. to about +30° C. The aforesaid process can be conducted for a period from about 1 hour to about 24 hours; preferably about 3 hours.

Suitable leaving groups L of the aforesaid compound of formula III of the aforesaid conversion include hydroxy, halo, azido, mono($C_{1-6}$alkyl)carbonate, ($C_{1-6}$alkyl)carboxylate, ($C_{6-10}$aryl)carboxylate, mono-($C_{6-10}$aryl)($C_{1-6}$alkyl)carboxylate, di-($C_{6-10}$aryl)($C_{6-10}$alkyl)carboxylate, di($C_{1-6}$alkyl)phosphorothioate, ($C_{1-6}$alkyl)sulfonyl, mono-($C_{1-6}$alkyl)($C_{6-10}$aryl)sulfonyl, di-($C_{1-6}$alkyl)($C_{6-10}$aryl)sulfonyl, ($C_{1-6}$alkyl)-(CO)—S—, cyano-$C_{1-6}$alkoxy, $C_{6-10}$aryloxy, 3-benzthiazolyloxy, 8-quinolinyloxy or N-oxy-succinimidyl.

In one embodiment of the aforesaid conversion of the invention, the leaving group L of the compound of formula III is selected from the group consisting of hydroxy, halo and azido.

In another embodiment of the aforesaid conversion of the invention, the leaving group L of the compound of formula III is selected from the group consisting of mono($C_{1-6}$alkyl)carbonate, ($C_{1-6}$alkyl)carboxylate, ($C_{6-10}$aryl)carboxylate, mono-($C_{6-10}$aryl)($C_{1-6}$alkyl)carboxylate, di-($C_{6-10}$aryl)($C_{1-6}$alkyl)carboxylate and di($C_{1-6}$alkyl)phosphorothioate.

In yet another embodiment of the aforesaid conversion of the invention, the leaving group L of the compound of formula III is selected from the group consisting of ($C_{1-6}$alkyl)sulfonyl, mono-($C_{1-6}$alkyl)($C_{6-10}$aryl)sulfonyl, di-($C_{1-6}$alkyl)($C_{6-10}$aryl)sulfonyl and ($C_{1-6}$alkyl)-(CO)—S—.

In yet another embodiment of the aforesaid conversion of the invention, the leaving group L of the compound of formula III is selected from the group consisting of cyano-$C_{1-6}$alkoxy, $C_{6-10}$aryloxy, 3-benzthiazolyloxy, 8-quinolinyloxy and N-oxy-succinimidyl.

In yet another embodiment of the aforesaid conversion of the invention, the leaving group L of the compound of formula III is selected from the group consisting of halo, methanesulfonyl, diethylphosphorothioate and 3-benzthiazolyloxy.

In a preferred embodiment of the aforesaid conversion of the invention, the leaving group L of the compound of formula III is di($C_{1-6}$alkyl)phosphorothioate, more preferably diethylphosphorothioate.

The present invention also relates to an alternative process for the preparation of the above 3-cyclic-ether-substituted cephalosporin of the formula I, or the pharmaceutically acceptable salts thereof, comprising reacting a compound of formula V

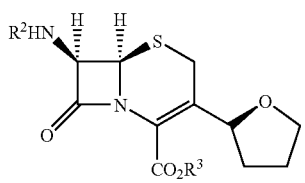

V wherein
$R^2$ has the formula

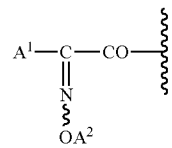

wherein
$A^1$ is $C_{6-10}$aryl, $C_{1-10}$heteroaryl or $C_{1-10}$heterocyclyl;
$A^2$ is hydrogen, $C_{1-6}$alkyl, $C_{3-10}$cycloalkyl, $C_{3-10}$cycloalkenyl, $C_{6-10}$aryl, $C_{1-6}$alkyl(CO)($C_{1-6}$)alkyl-O—, HO(CO)($C_{1-6}$)alkyl, mono-($C_{6-10}$aryl)($C_{1-6}$alkyl), di-($C_{6-10}$aryl)($C_{1-6}$alkyl) or tri-($C_{6-10}$aryl)($C_{1-6}$alkyl); and $R^3$ is para-nitrobenzyl or allyl, preferably allyl; with a suitable deprotecting agent in the presence of a solvent.

The term "alkyl", as used herein, unless otherwise indicated, includes saturated monovalent hydrocarbon radicals having straight, branched moieties or combinations thereof. alkyl groups, wherever they occur, may be optionally substituted by a suitable substituent.

The term "cycloalkyl", as used herein, unless otherwise indicated, includes a mono or bicyclic carboxcyclic ring (e.g., cyclopropyl, cyclobutyl, cyclopentyl, cyclohexyl, cycloheptal, cyclooctyl, cyclononyl, bicyclo[2.2.1]heptanyl, bicyclo[3.2.1]octanyl and bicyclo[5.2.0]nonanyl, etc.); optionally substituted by 1 to 3 suitable substituents as defined below such as fluoro, chloro, trifluoromethyl, ($C_{1-4}$)alkoxy, ($C_{6-10}$)aryloxy, trifluoromethoxy, difluoromethoxy or ($C_{1-4}$)alkyl, more preferably fluoro, chloro, methyl, ethyl or methoxy.

The term "cycloalkenyl," as used herein, unless otherwise indicated, includes a monocarbocyclic ring (e.g., cyclopentenyl, cyclohexenyl, cycloheptenyl, cyclooctenyl, cyclononenyl, etc.) optionally substituted by 1 to 3 suitable substituents as defined below such as fluoro, chloro, trifluoromethyl, ($C_{1-4}$)alkoxy, ($C_{6-10}$)aryloxy trifluoromethoxy, difluoromethoxy or ($C_{1-4}$)alkyl, more preferably fluoro, chloro, methyl, ethyl or methoxy.

The term "alkoxy", as used herein, includes O-alkyl groups wherein "alkyl" is as defined above.

The term "halo", as used herein, unless otherwise indicated, includes fluorine, chlorine, bromine or iodine, preferably bromine or chlorine.

The term "aryl", as used herein, unless otherwise indicated, includes an organic radical derived from an aromatic hydrocarbon by removal of one or more hydrogen(s), such as phenyl or naphthyl, optionally substituted by 1 to 3 suitable substituents such as fluoro, chloro, cyano, nitro, trifluoromethyl, ($C_{1-6}$)alkoxy, ($C_{6-10}$)aryloxy, ($C_{3-8}$)cycloalkyloxy, trifluoromethoxy, difluoromethoxy or ($C_{1-6}$) alkyl.

The term "heteroaryl", as used herein, unless otherwise indicated, includes an organic radical derived from an aromatic heterocyclic compound by removal of one or more hydrogen(s), such as benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_{1-10})$heteroaryl is optionally substituted on any of the ring carbon atoms capable of forming an additional bond by one or two substituents independently selected from F, Cl, Br, CN, OH, $(C_{1-4})$alkyl, $(C_{1-4})$perfluoroalkyl, $(C_{1-4})$perfluoroalkoxy, $(C_{1-4})$alkoxy and $(C_{3-8})$cycloalkyloxy. The foregoing groups, as derived from the compounds listed above, can be C-attached or N-attached where such is possible. For instance, a group derived from pyrrole can be pyrrol-1-yl (N-attached) or pyrrol-3-yl (C-attached).

The term "heterocyclyl", as used herein, unless otherwise indicated, includes an organic radical derived from a non-aromatic heterocyclic compound by removal of one or more hydrogens, such as 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydropyranyl, tetrahydropyranyl, 1,2,3,6-tetrahydropyridinyl, tetrahydrothienyl, tetrahydrothiopyranyl, thiomorpholinyl, thioxanyl and trithianyl. The foregoing groups, as derived from the compounds listed above, can be C-attached or N-attached where such is possible. For example, a group derived from piperidine can be piperidin-1-yl (N-attached) or piperidin-4-yl (C-attached). The foregoing groups, as derived from the compounds listed above, can be optionally substituted where such is possible by a suitable substituent, such as oxo, F, Cl, Br, CN, OH, $(C_{1-4})$alkyl, $(C_{1-4})$perfluoroalkyl, $(C_{1-4})$perfluoroalkoxy, $(C_{1-4})$alkoxy, or $(C_{3-8})$cycloalkyloxy.

The phrase "a suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like.

The term "carboxylate salt", as used herein, includes metal salts (such as aluminium, alkali metal salts, such as sodium or potassium, preferably sodium), alkaline earth metal salts (such as calcium or magnesium), and ammonium salts. The ammonium salts can be substituted with $C_{1-6}$alkylamines (such as triethylamine), hydroxy-$(C_{1-6})$alkylamines (such as 2-hydroxyethylamine, bis-(2-hydroxyethyl)amine, or tris-(2-hydroxyethyl)amine), cycloalkylamines (such as dicyclohexylamine), procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bis-dehydro-abietylamine, ethylenediamine, or pyridine-type bases (such as pyridine, collidine or quinoline), or other amines which have been used to form salts with known penicillins and 3-cyclic-ether-substituted cephalosporins. Other useful salts include the lithium salt and silver salt. Salts within compounds of formula I can be prepared by salt exchange in conventional manner.

The term "active compounds", as used herein, refers to compounds of formula I.

Compounds of formula I contain chiral centers and therefore exist in different enantiomeric forms. This invention relates to all optical isomers, enantiomers, diastereomers and stereoisomers of the compounds of formula I and mixtures thereof. The compounds of the invention also exist in different tautomeric forms. This invention relates to all tautomers of formula I. Those skilled in the art are well aware that the cephalosporin nucleus exists as a mixture of tautomers in solution. The various ratios of the tautomers in solid and liquid form is dependent on the various substituents on the molecule as well as the particular crystallization technique used to isolate a compound.

Preferably, the group $OA^2$ of said compounds of formula III is cis to the amide linkage, i.e., the Z-configuration is preferred.

Suitable deprotecting agents for the aforesaid process of conversion of compounds of formula V into compounds of formula I of the invention include sodium dithionite or tetrakis triphenyl phosphine palladium (0).

Suitable solvents for the aforesaid conversion include acetone, water, tetrahydrofuran, methylene chloride or mixtures thereof. In one embodiment of the invention, the solvent is methylene chloride, tetrahydrofuran or mixtures thereof. In another embodiment of the invention, the solvent is tetrahydrofuran. In a preferred embodiment of the aforesaid conversion of the invention, the solvent is methylene chloride.

The aforesaid conversion may be conducted at a temperature of about 0° C. to about 45° C. The aforesaid conversion may be conducted for a period from about 1 hour to about 24 hours.

In one embodiment of the aforesaid conversion, $R^3$ is para-nitrobenzyl. Within, this embodiment, suitably the deprotecting agent is sodium dithionite. Within this embodiment, suitably the aforesaid conversion is conducted at a temperature of about 40° C. Within this embodiment, suitably the aforesaid process is conducted for about 4 hours.

In a preferred embodiment of the aforesaid conversion, $R^3$ is allyl. Within this -embodiment, the preferred deprotecting agent is tetrakis triphenyl phosphine palladium (0). Within this embodiment, the aforesaid process is conducted at a temperature of about 20° C. to about 35° C.; preferably about 27° C. to about 30° C. Within this embodiment, preferably the aforesaid process is conducted for about 5 hours.

The present invention also includes a process for the preparation of the above compound of formula II comprising reacting a compound of formula IV

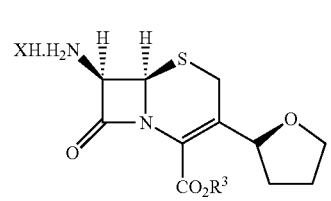

IV wherein $R^3$ is para-nitrobenzyl or allyl, preferably para-nitrobenzyl; and X is halo, preferably chloro; with a suitable deprotecting agent; in the presence of a solvent.

Suitable solvents for the process of conversion of compounds of formula IV into compounds of formula II of the invention include acetone, water, tetrahydrofuran, methylene chloride or mixtures thereof. In one embodiment of the invention, the solvent is acetone, water, tetrahydrofuran or mixtures thereof. Preferably, the solvent is a mixture of acetone and, water. More preferably, the-solvent is a 3:1 mixture of acetone and water.

Suitable deprotecting agents for the aforesaid conversion include sodium dithionite, catalytic hydrogenating agent (such as hydrogen gas over 10% palladium over carbon) or tetrakis triphenyl phosphine palladium (0).

The aforesaid conversion may be conducted at a temperature of about 0° C. to about 45° C. The aforesaid conversion may be conducted for a period from about 1 hour to about 24 hours.

In the preferred embodiment of the aforesaid conversion, $R^3$ is para-nitrobenzyl. Within this embodiment, the preferred deprotecting agent is sodium dithionite. Preferably, the aforesaid process is conducted at a temperature of about 45° C. Preferably, the aforesaid process is conducted at a temperature of about 1 hour.

In another embodiment of the invention, $R^3$ is allyl. Within this embodiment, suitably the deprotecting agent is tetrakis triphenyl phosphine palladium (0). Suitable solvents include methylene chloride and tetrahydrofuran. The aforesaid process can be conducted at a temperature of about 20° C. to about 35° C.

The present invention also relates to a process for the preparation of the above compound of formula V comprising reacting the above compound of formula IV, wherein $R^3$ is para-nitrobenzyl or allyl; preferably allyl; and X is halo; preferably chloro; with a compound of the formula III, as defined above, in the presence of a solvent. Optionally, the aforesaid process can be conducted in the presence of an optional coupling agent or an optional catalyst.

Suitable solvents for the aforesaid conversion of compounds of formula IV into compounds of formula V include methylene chloride, tetrahydrofuran or mixtures thereof.

In one embodiment of the aforesaid conversion of the invention, a coupling agent is used. Within this embodiment, suitable coupling agents include N,N'-diethylcarbodiimide, N,N'-dipropyl carbodiimide, N,N'-diisopropylcarbodiimide, N,N'-dicyclohexylcarbodiimide, N-ethyl N'-[3-(dimethylamino)propyl]carbodiimide, N,N'-carbonyldiimidazole or N,N'-carbonyldithiazole. A preferred coupling agent is N,N'-dicyclohexylcarbodiimide. Preferably, the aforesaid conversion is conducted in the absence of any coupling agents.

In another embodiment of the aforesaid conversion of the invention, a catalyst is used. Within this embodiment, the catalyst can be a Lewis acid. Suitable Lewis acids are boron trihalide, such as boron tribromide, or aluminum halide, such as aluminum chloride. Preferably, the aforesaid conversion is conducted in the absence of any catalysts.

The aforesaid conversion may be conducted at a temperature of about −40° C. to about +40° C. The aforesaid conversion may be conducted for a period of from about 1 hour to about 24 hours.

In one embodiment of the aforesaid conversion of the invention, $R^3$ is para-nitrobenzyl. Within this embodiment, suitably the aforesaid conversion is conducted at a temperature of about +20° C. to about +30° C. Within this embodiment, suitably the aforesaid conversion is conducted for about 3 hours.

In a preferred embodiment of the aforesaid conversion of the invention, $R^3$ is allyl. Within this embodiment, preferably the solvent is methylene chloride. Within this embodiment, preferably the aforesaid conversion is conducted at a temperature of about 20° C. to about 40° C. Within this embodiment, preferably the aforesaid conversion is conducted for about 24 hours.

Suitably the leaving group L of the compound of formula III in the aforesaid conversion of the invention includes hydroxy, halo, azido, mono($C_{1-6}$alkyl)carbonate, ($C_{1-6}$alkyl)carboxylate, ($C_{6-10}$aryl)carboxylate, mono-($C_{6-10}$aryl)($C_{1-6}$alkyl)carboxylate, di-($C_{6-10}$aryl)($C_{1-6}$alkyl)carboxylate, di($C_{1-6}$alkyl)phosphorothioate, ($C_{1-6}$alkyl)sulfonyl, mono-($C_{1-6}$alkyl)($C_{6-10}$aryl)sulfonyl, di-($C_{1-6}$alkyl)($C_{6-10}$aryl)sulfonyl, ($C_{1-6}$alkyl)-(CO)—S—, cyano-$C_{1-6}$alkoxy, $C_{6-10}$aryloxy, 3-benzthiazolyloxy, 8-quinolinyloxy or N-oxy-succinimidyl.

In one embodiment of the aforesaid conversion of the invention, the leaving group L of the compound of formula III is selected from the group consisting of hydroxy, halo and azido.

In another embodiment of the aforesaid conversion of the invention, the leaving group L of the compound of formula III is selected from the group consisting of mono($C_{1-6}$alkyl)carbonate, ($C_{1-6}$alkyl)carboxylate, ($C_{6-10}$aryl)carboxylate, mono-($C_{6-10}$aryl)($C_{1-6}$alkyl)carboxylate, di-($C_{6-10}$aryl)($C_{1-6}$alkyl)carboxylate and di($C_{1-6}$alkyl)phosphorothioate.

In yet another embodiment of the aforesaid conversion of the invention, the leaving group L of the compound of formula III is selected from the group consisting of ($C_{1-6}$alkyl)sulfonyl, mono-($C_{1-6}$alkyl)($C_{6-10}$aryl)sulfonyl, di-($C_{1-6}$alkyl)($C_{6-10}$aryl)sulfonyl and ($C_{1-6}$alkyl)-(CO)—S—.

In yet another embodiment of the aforesaid conversion of the invention, the leaving group L of the compound of formula III is selected from the group consisting of cyano-$C_{1-6}$alkoxy, $C_{6-10}$aryloxy, 3-benzthiazolyloxy, 8-quinolinyloxy and N-oxy-succinimidyl.

In yet another embodiment of the aforesaid conversion of the invention, the leaving group L of the compound of formula III is selected from the group consisting of halo, methanesulfonyl, diethylphosphorothioate and 3-benzthiazolyloxy.

In a preferred embodiment of the aforesaid conversion of the invention, the leaving group L of the compound of formula III is mono($C_{1-6}$alkyl)carbonate, more preferably acetate.

The present invention also relates to a compound of formula II

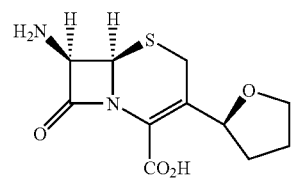

II

In one embodiment of the invention, the compound of formula II has an enantiomeric or diastereomeric purity of 96% to 100%; preferably 97%.

The present invention also relates to a compound of formula V

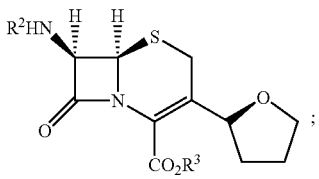

wherein $R^2$ is as defined above; and $R^3$ is para-nitrobenzyl or allyl; preferably allyl.

In one embodiment of the invention, the compound of formula V has an enantiomeric or diastereomeric purity of 96% to 100%; preferably 97%.

In generic or sub-generic embodiments of each of the foregoing embodiments, the $A^1$ moiety of said $R^2$ is $C_{6-10}$aryl, such as phenyl. In other generic or sub-generic embodiments of the invention, the $A^1$ moiety of said $R^2$ is $C_{1-10}$heteroaryl selected from the group consisting of furyl, thienyl, pyridyl, aminothiazolyl and aminothiadiazolyl, in which the amino moiety of said aminothiazolyl or aminothiadiazolyl is optionally protected. In other generic or sub-generic embodiments of the invention, the $A^1$ moiety of said $R^2$ is $C_{1-10}$heterocyclyl; such as 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Preferably the $A^1$ moiety of said $R^2$ is aminothiazolyl.

In other generic or sub-generic embodiments of the invention, the $A^2$ moiety of said $R^2$ is hydrogen or $C_{1-6}$alkyl. A preferred embodiment of the invention includes each of the foregoing generic and sub-generic embodiments wherein the $A^2$ moiety of said $R^2$ is $C_{1-6}$alkyl, more preferably methyl.

In a preferred embodiment of each of the foregoing generic and sub-generic embodiments the invention, a compound of the formula III has a formula IIIa

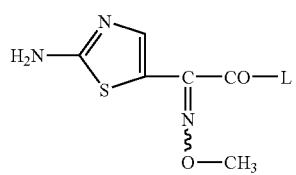

(IIIa)

wherein L is a leaving group, such as halo, methanesulfonyl, dialkylphosphorothioate, such as diethylphosphorothioate or 3-benzthiazolyloxy.

In a most preferred embodiment of each of the foregoing embodiments of the invention, a compound of the formula III has a formula IIIa, as defined above, wherein L is diethylphosphorothioate or acetate.

The optional conversion of $R^2$ to a different $R^2$ and the optional formation of a pharmaceutically acceptable salt, can be carried out using methods well known in the art.

In the processes described hereinabove and hereinbelow, it may be necessary to remove protecting groups. Deprotection can be carried out by any convenient method known in the art such that unwanted side reactions are minimized. Separation of unwanted by-products can be carried out using standard methods known to those skilled in the art (for example, see "Protection of the Amino Group", in *Protective Groups in Organic Synthesis,* 2nd Edition, T. W. Greene and P. G. M. Wuts, Ed., Wiley and Sons, Inc. 1991, pp. 309–405).

The present invention also relates to a method of using a zwitterion intermediate for the preparation of 3-cyclic-ether-substituted cephalosporins.

DETAILED DESCRIPTION OF THE INVENTION

The process of the present invention and the preparation of the compound of the present invention are illustrated in the following reaction schemes. Except where otherwise indicated, in the reaction schemes and discussion that follow, substituents $R^1$, $R^2$, $R^3$, L, $A^1$, $A^2$ and X are as defined above unless otherwise described.

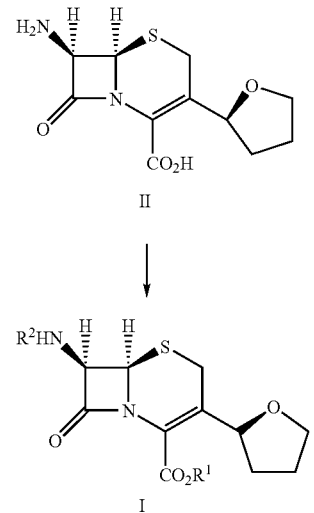

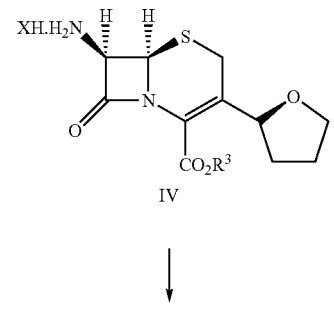

-continued
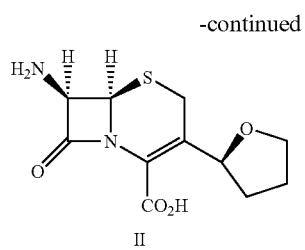
II
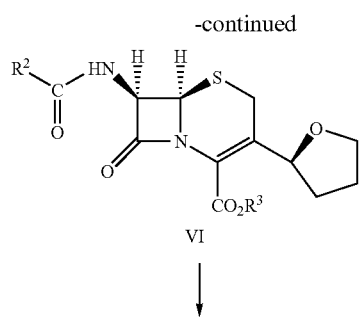
VI
SCHEME 3
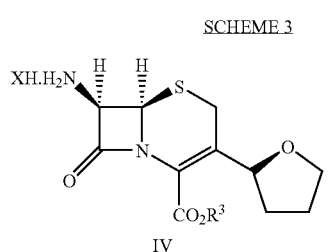
IV
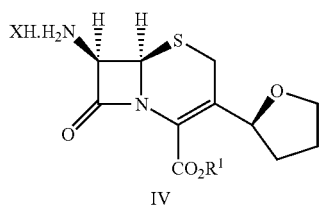
IV
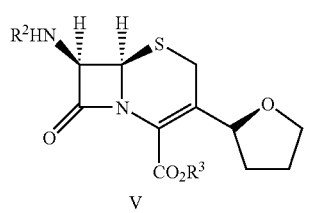
V
SCHEME 5
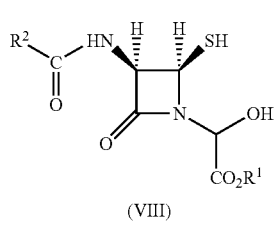
(VIII)
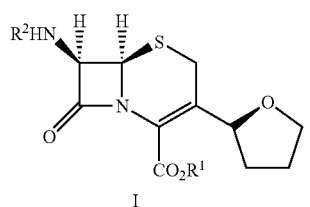
I
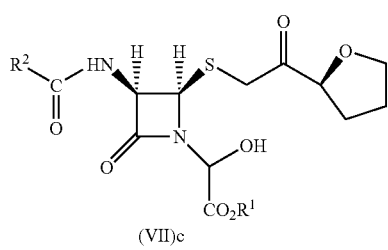
(VII)c
SCHEME 4
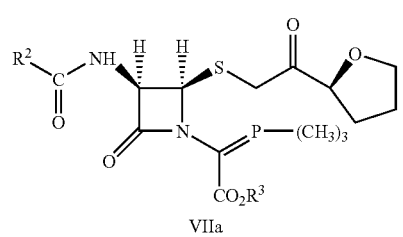
VIIa
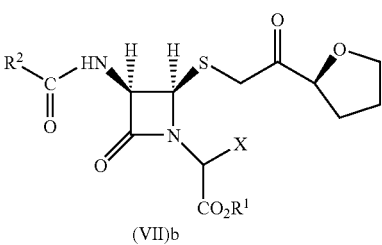
(VII)b -continued

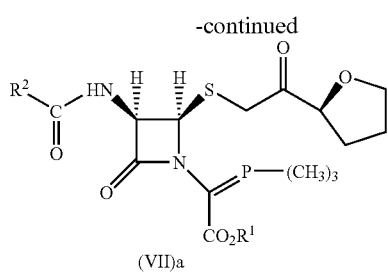
(VII)a wherein L is a leaving group, in the presence of a base and a solvent.

Suitable leaving groups include hydroxy, halo, azido, mono($C_{1-6}$alkyl)carbonate, ($C_{1-6}$alkyl)carboxylate, ($C_{6-10}$aryl)carboxylate, mono-($C_{6-10}$aryl)($C_{1-6}$alkyl)carboxylate, di-($C_{6-10}$aryl)($C_{1-6}$alkyl)carboxylate, di($C_{1-6}$alkyl)phosphorothioate, ($C_{1-6}$alkyl)sulfonyl, mono-($C_{1-6}$alkyl)($C_{6-10}$aryl)sulfonyl, di-($C_{1-6}$alkyl)($C_{6-10}$aryl)sulfonyl, ($C_{1-6}$alkyl)-(CO)—S—, cyano-$_{1-6}$alkoxy, $C_{6-10}$aryloxy, 3-benzthiazolyloxy, 8-quinolinyloxy or N-oxy-succinimidyl. Preferably, the leaving group is di($C_{1-6}$alkyl)phosphorothioate, such as diethylphosphorothioate.

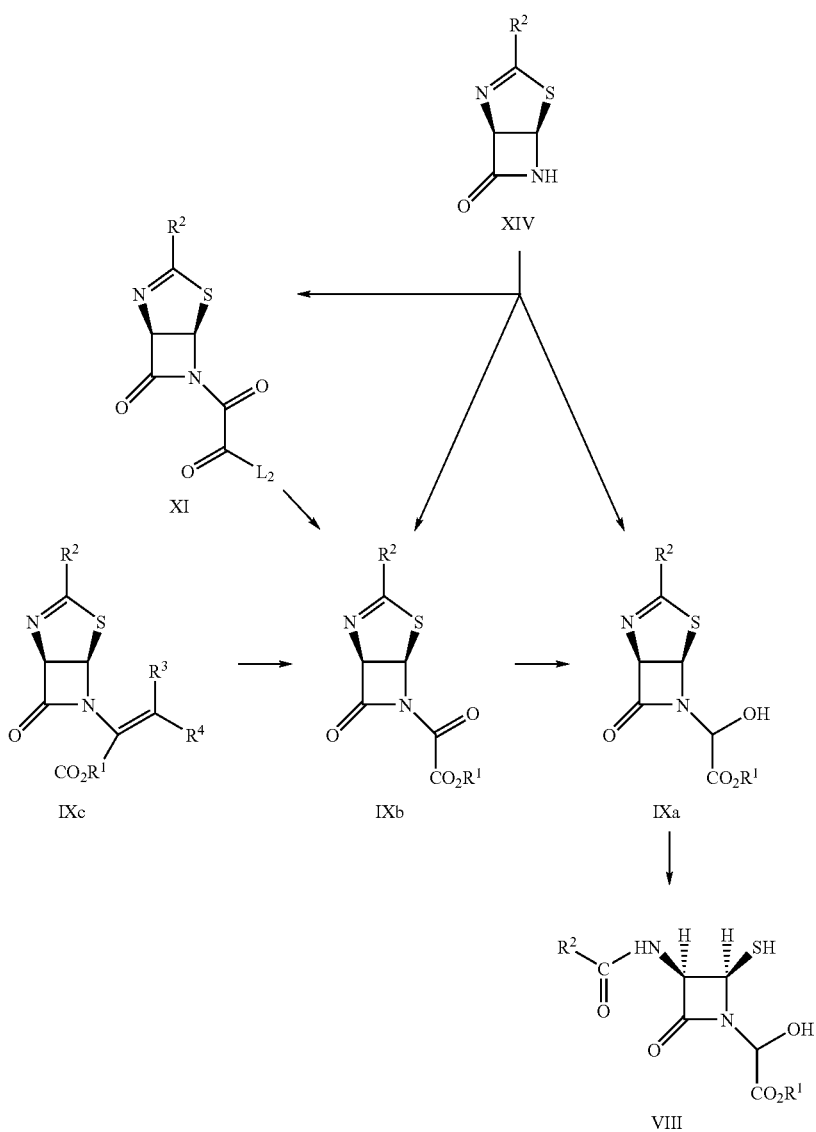

Scheme 1 refers to the preparation of compounds of formula I. Referring to Scheme 1, a compound of formula I can be prepared by reacting a compound of formula II with a compound of formula III $R^2$-L  (III)

Suitable bases include diisopropylethylamine or sodium hydroxide, preferably sodium hydroxide, most preferably 15% aqueous sodium hydroxide.

Suitable solvents include water, acetone, tetrahydrofuran, ethyl acetate, dimethylacetamide, dimethylformamide, acetonitrile, methylene chloride, 1,2-dichloroethane, or mixtures thereof; preferably a mixture of water and acetone, most preferably a mixture of 1:1.3 of water and acetone.

The aforesaid reaction can be conducted at a temperature of about −40° C. to about 30° C.; preferably about 20° C. to about 30° C. The aforesaid reaction can be conducted for a period from about 1 hour to about 24 hours, preferably for about 3 hours.

Optionally, the aforesaid reaction can be effected in the presence of an acid binding agent, for example a tertiary amine (such as triethylamine), pyridine (such as 2,6-lutidine or 4-dimethylaminopyridine), or dimethylaniline. Optionally, the aforesaid reaction can also be carried out in the presence of molecular sieves, an inorganic base (such as calcium carbonate or sodium bicarbonate) or an oxirane, which binds the hydrogen gas liberated in the aforesaid reaction. The oxirane is preferably $C_{1-6}$alkyl-1,2-alkylene oxide, such as ethylene oxide or propylene oxide.

Optionally, the aforesaid reaction can be conducted in the presence of a coupling agent. Suitable coupling agents include N,N'-diethylcarbodiimide, N,N'-dipropyl carbodiimide, N,N'-diisopropylcarbodiimide, N,N'-dicyclohexylcarbodiimide, N-ethyl-N'-[3-(dimethylamino)propyl]carbodiimide, N,N'-carbonyldiimidazole, and N,N'-carbonyldithiazole. Preferably, the coupling agent is N,N'-diethylcarbodiimide. Preferably the reaction is conducted in the absence of any couplings agents.

Optionally, the aforesaid reaction can be conducted in the presence of a catalyst. Suitable catalysts include a Lewis acid, such as boron trihalide or aluminum halide. Preferably the reaction is conducted in the absence of any catalysts.

The compound of formula III can be prepared by methods known in the art. Suitable methods include those described, for example, in U.K. Patent No. 2 107 307 B, U.K. Patent Specification No. 1,536,281 and U.K. Patent Specification No. 1,508,064. Preferably, the compound of formula III (i.e. $R^2L$), wherein $R^2$ has a formula:

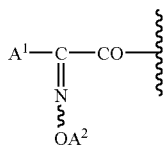

wherein A is 2-aminothiazol-4-yl, $A^2$ is methyl, and L is $(C_{1-6}$alkyl)sulfonyl, such as methylsulfonyl, or di$(C_{1-6}$alkyl) phosphorothioate, such as diethylphosphorothioate, can be prepared by reacting a compound of formula IIIb

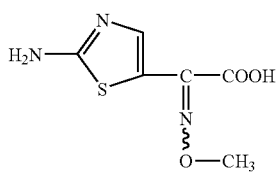

with $(C_{1-6}$alkyl)sulfonylhalide, such as methanesulfonylchloride, or di$(C_{1-6}$alkyl)thiophosphonic acid, such as diethylthiophoshonic acid.

Most preferably, the compound of formula III is diethylthiophoshoryl-[Z]-2-aminothiazol-4-yl-methoxylamino (DAMA), which can be prepared according to the methods described in U.S. Pat. No. 5,567,813 and EP 628561.

Scheme 2 refers to the preparation of a compound of formula II. Referring to Scheme 2, a compound of formula II can be prepared by reacting a compound of formula IV, wherein $R^3$ preferably para-nitrobenzyl ester; and X is preferably chloro; with a suitable deprotecting agent in a solvent.

Suitable deprotecting agents include sodium dithionite or a catalytic hydrogenating agent, such as hydrogen gas over 10% palladium on carbon.

Suitable solvents include acetone, water, tetrahydrofuran, methylene chloride or mixtures thereof. Preferably the solvent is a mixture of 3:1 acetone and water.

The aforesaid reaction can be conducted at a temperature of about 0° C. to about 45° C., preferably about 45° C. The aforesaid reaction can be conducted for a period from about 1 hour to about 24 hours, preferably from about 1 hour.

A compound of formula IV can be prepared by various synthetic methods such as those described in the United States Non-Provisional Patent Application entitled "Process and Ester Derivatives Useful For Preparation of Cephalosporins", filed Dec. 4, 2001. These methods are described hereinbelow in Schemes 4–6.

Scheme 3 refers to an alternative process of preparation of a compound of formula I. Referring to Scheme 3, a compound of formula I can be prepared by reacting a compound of formula V, wherein $R^3$ is preferably allyl; with a suitable deprotecting agent in a solvent.

Suitable deprotecting agents include sodium dithionite or tetrakistriphenyl phosphine palladium (0).

Suitable solvents include acetone, water, tetrahydrofuran, methylene chloride or mixtures thereof. Preferably the solvent is methylene chloride.

The aforesaid reaction can be conducted at a temperature of about 0° C to about 45° C. The aforesaid reaction can be conducted for a period from about 1 hour to about 24 hours.

A compound of formula V can be prepared by reacting a compound of formula IV, wherein $R^3$ is preferably allyl; and X is preferably chloro; with a compound of formula III $$R^2\text{-L} \qquad (III)$$

in a solvent.

Suitable solvents for the aforesaid reaction include methylene chloride, tetrahydrofuran or mixtures thereof. Preferably, the solvent is methylene chloride.

Optionally, the aforesaid reaction can be conducted in the presence of a coupling agent. Suitable coupling agents include N,N'-diethylcarbodiimide, N,N'-dipropyl carbodiimide, N,N'-diisopropylcarbodiimide, N,N'-dicyclohexylcarbodiimide, N-ethyl-N'-[3-(dimethylamino)propyl]carbodiimide, N,N'-carbonyldiimidazole, or N,N'-carbonyldithiazole. Preferably, the coupling agent is N,N'-diethylcarbodiimide. Preferably the aforesaid reaction is conducted without any coupling agents.

Optionally, the aforesaid reaction can be conducted in the presence of a catalyst. Suitable catalysts include a Lewis acid, such as boron trihalide or aluminum halide. Preferably the aforesaid reaction is conducted without any catalysts.

The aforesaid reaction can be conducted at a temperature of about −40° C. to about +40° C., preferably about +20° C. to about +40° C. The aforesaid reaction can be conducted for a period from about 1 hour to about 24 hours; preferably about 24 hours.

A compound of formula IV can be prepared as described below in the description for Schemes 4–6.

Scheme 4 refers to the preparation of a compound of formula (IV). Referring to Scheme 4, a compound of formula (IV) wherein $R^1$ is preferably para-nitrobenzyl can be prepared by reaction of a compound of formula (VI) wherein $R^1$ is preferably para-nitrobenzyl, and $R^2$ is preferably $C_{6-10}arylC_{1-6}alkyl$, such as benzyl, with an acid in a solvent. Suitable acids include Lewis Acids, such as phosphorus pentachloride or phosphorus pentabromide, preferably phosphorus pentachloride. Suitable solvents include toluene, xylene, tetrahydrofuran, methylene chloride or acetonitrile; preferably methylene chloride. The aforesaid process can be conducted at a temperature of about −40° C. to about +40° C. The aforesaid process is conducted for a period of from about 1 hour to about 24 hours.

A compound of formula (VI) wherein $R^1$ is preferably para-nitrobenzyl, and $R^2$ is preferably $C_{6-10}arylC_{1-6}alkyl$, such as benzyl, can be prepared by cyclizing a compound of formula (VIIa), wherein $R^1$ is preferably para-nitrobenzyl; and $R^2$ is preferably $C_{6-10}arylC_{1-6}alkyl$, such as benzyl; by heating said compound of formula (VIIa) in a solvent.

The aforesaid process for the conversion of compounds of formula (VIIa) into compounds of formula (VI) is a so called intramolecular Wittig-type reaction and is typically conducted by heating the above compound of formula (VIIa). Suitable solvents include toluene, xylene, tetrahydrofuran, methylene chloride and acetonitrile, preferably methylene chloride. The aforesaid process is conducted at a temperature of from about 40° C. to about 160° C. The aforesaid process is conducted for a period of from about 1 hour to about 24 hours, preferably about 16 hours.

The aforesaid conversion of the compound of formula (VIIa) to the compound of formula (IV) can be performed as a two step process in which the compound of formula (VI) may be isolated but is preferably carried out as a one step reaction without isolation of the phosphorus ylide.

Compounds of formula (VIIa) can be prepared by the methods of Scheme 5.

Scheme 5 refers to the preparation of compounds of the formula (VIIa), wherein $R^1$ is preferably para-nitrobenzyl; and $R^2$ is preferably $C_{6-10}arylC_{1-6}alkyl$, such as benzyl; by the processes of the present invention. Compounds of the formula (VIIa) are intermediates useful in the preparation of compounds of formula (IV) in Scheme 4.

Referring to Scheme 5, the aforesaid compound of formula (VIIa) can be prepared by reacting a compound of formula (VIIb), wherein $R^1$ is preferably para-nitrobenzyl; and $R^2$ is preferably $C_{6-10}arylC_{1-6}alkyl$, such as benzyl; and X is preferably chloro, with trimethylphoshine, in a solvent, optionally in the presence of a suitable base.

Suitable solvents include tetrahydrofuran, acetonitrile and methylene chloride, preferably tetrahydrofuran. Suitable bases include imidazole, 2,6-lutidine, pyridine, N-methymorpholine or sodium bicarbonate, preferably sodium bicarbonate. Preferably the reaction is conducted with the suitable base during work up. The aforesaid process is conducted at a temperature of from about −40° C. to about −20° C. The aforesaid process is conducted for a period of from about 30 minutes to about 1 hour.

A compound of formula (VIIb), wherein $R^1$ is preferably para-nitrobenzyl; and $R^2$ is preferably $C_{6-10}arylC_{1-6}alkyl$, such as benzyl; can be prepared by reacting a compound of formula (VIIc), wherein $R^1$ is preferably para-nitrobenzyl; and $R^2$ is preferably $C_{6-10}arylC_{1-6}alkyl$, such as benzyl; with a halogenating agent in the presence of a base in a solvent. Suitable halogenating agents include thionyl chloride, thionyl bromide, phosphorus tribromide or phosphorus trichloride, preferably thionyl chloride. Suitable bases include pyridine, 2,6-lutidine, N-methylmorpholine or imidazole, preferably 2,6-lutidine. Suitable solvents include tetrahydrofuran or methylene chloride, preferably methylene chloride. The aforesaid process is conducted at a temperature of from about −40° C. to about −20° C., preferably about −20° C. The aforesaid process is conducted for a period of from about 15 minutes to about 1 hour, preferably about 1 hour.

A compound of formula (VIIc), wherein $R^1$ is preferably para-nitrobenzyl; and $R^2$ is preferably $C_{6-10}arylC_{1-6}alkyl$, such as benzyl; can be prepared by reacting a compound of formula (IX), wherein $R^1$ is preferably para-nitrobenzyl; and $R^2$ is preferably $C_{6-10}arylC_{1-6}alkyl$, such as benzyl; with a compound of formula (VIII)

(VIII)

wherein Y is a leaving group such as bromo, chloro, fluoro, iodo or tosylate, preferably bromo, in a solvent. Suitable solvents include alcohol, such as methanol, ethanol and propanol; methylene chloride; acetone; dimethylformamide; or mixtures thereof. The aforesaid process is conducted at a temperature of from about 10° C. to about 25° C. The aforesaid process is conducted for a period of from about 4 hours to about 24 hours.

Compounds of formula (VIII) are known compounds and can be prepared by standard methodology. For example, compounds of formula (VIII), in which Y is chloro or bromo, can be prepared from a compound of formula (VIIIa)

(VIIIa)

by reacting said compound of formula (VIIIa) with a halogenating agent, such as thionyl chloride or phophorus tribromide, to form the corresponding acid halide (such as chloroformyltetrahydrofuran or bromoformyltetrahydrofuran). Said acid halide is reacted with diazomethane to form a diazo compound. The resulting diazo compound is then treated with hydrogen chloride or hydrogen bromide to form the corresponding compound of formula (VIII).

Compounds of formula (VIIIa), the corresponding acid halides and diazomethane are commercially available.

Alternatively, the compound of formula (VIII) can be prepared in situ by reacting the corresponding carboxylic acid of formula (VIIIb)

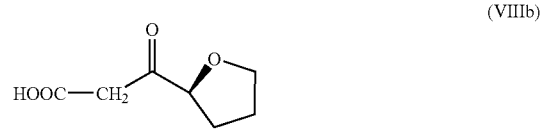

(VIIIb)

with a halogenating agent in methanol or water solution; and subsequently exposing the solution to an acid, preferably para-toluene sulfonic acid. Suitable halogenating agents include bromine, chlorine or iodine, preferably bromine.

Those skilled in the art would understand that in the process of the invention, the compound of formula (VIII) made in situ is then reacted with compounds of formula (IX) to prepare compounds of formula (VIIc), by the method described above.

Compounds of the formula (IX) can be prepared by the methods of Scheme 6.

Scheme 6 refers to the preparation of compounds of the formula (IX), wherein $R^1$ is preferably para-nitrobenzyl; and $R^2$ is preferably $C_{6-10}arylC_{1-6}alkyl$, such as benzyl; by the processes of the present invention. Compounds of the formula (IX) are useful intermediates in the preparation of compounds of formula (IV), via compounds of the formula (VIIa). The conversion of compounds of formula (IX) into compounds of formula I are described in Schemes 1 and 2. Referring to Scheme 6, a compound of formula (IX) can be prepared by reacting a compound of formula (Xa), wherein $R^1$ is preferably para-nitrobenzyl; and $R^2$ is preferably $C_{6-10}arylC_{1-6}alkyl$, such as benzyl; with an acid in a solvent. Suitable acids include para-toluene sulfonic acid and methane sulfonic acid, preferably para-toluene sulfonic acid. Suitable solvents include methylene chloride, tetrahydrofuran, acetone or mixtures thereof, preferably methylene chloride. The aforesaid process is conducted at a temperature of from about 20° C. to about 25° C. The aforesaid process is conducted for a period of from about 2 hours to about 24 hours.

A compound of formula (Xa), wherein $R^1$ is preferably para-nitrobenzyl; and $R^2$ is preferably $C_{6-10}arylC_{1-6}alkyl$, such as benzyl; can be prepared by reacting a compound of formula (Xb), wherein $R^1$ is preferably para-nitrobenzyl; and $R^2$ is preferably.

$C_{6-10}arylC_{1-6}alkyl$, such as benzyl; with a reducing agent; in a solvent. Suitable reducing agents include sodium borohydride, sodium cyanoborohydride, borane and sodium triacetoxy borohydride, preferably sodium triacetoxyborohydride or sodium borohydride. Suitable solvents include acetic acid, methylene chloride, tetrahydrofuran, alcohol (such as isopropanol) or mixtures thereof. When the reducing agent is sodium triacetoxy borohydride, preferably the solvent is methylene chloride. When the reducing agent is sodium borohydride, preferably the solvent is acetic acid. The aforesaid process is conducted at a temperature of from about 20° C. to about 66° C. The aforesaid process is conducted for a period of from about 4 hours to about 24 hours.

Alternatively, the compound of formula (Xa), wherein $R^1$ is preferably para-nitrobenzyl; and $R^2$ is preferably $C_{6-10}arylC_{1-6}alkyl$, such as benzyl; can be prepared by reacting a compound of formula (XV), wherein $R^2$ is preferably $C_{6-10}arylC_{1-6}alkyl$, such as benzyl, with a compound of formula (XIV),

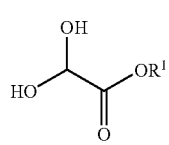

(XIV)

wherein $R^1$ is preferably para-nitrobenzyl, in the presence of a base in a solvent. Suitable bases include diisopropylamine, triethylamine, pyridine and 2,6-lutidine; preferably triethylamine; more preferably the triethylamine is catalytic. Suitable solvents include methylene chloride, tetrahydrofuran or mixtures thereof. The aforesaid process is conducted at a temperature of from about 20° C. to about 25° C. The aforesaid process is conducted for a period of from about 30 minutes to about 2 hours, preferably about 1 hour.

Compounds of formulae (XIV) and (XV) are individually known and are commercially available.

A compound of formula (XIVb), wherein $R^1$ is preferably para-nitrobenzyl; $R^2$ is preferably $C_{6-10}arylC_{1-6}alkyl$, such as benzyl; can be prepared by reacting a compound of formula (XII), wherein $R^2$ is preferably $C_{6-10}arylC_{1-6}alkyl$, such as benzyl, and said $L_2$ is halo, such as bromo or chloro, with a compound of formula (XI)

$$R^1—OH \quad (XI)$$

wherein $R^1$ is preferably para-nitrobenzyl; in a solvent, in the presence of a base.

Said compound of formula (XII) is prepared by reacting said compound of formula (XV) with a compound of formula (XIII)

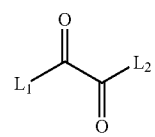

(XIII)

wherein each of $L_1$ and $L_2$ is a leaving group, such as halo, preferably chloro, in a solvent, optionally in the presence of a base. Suitable solvents include methylene chloride, tetrahydrofuran, or mixtures thereof, preferably methylene chloride. Suitable bases include diisopropylamine, triethylamine, pyridine and 2,6-lutidine, preferably triethylamine. The aforesaid process is conducted at a temperature of about −78° C. to about 25° C., preferably about −78° C. The aforesaid process is conducted for a period of from about 5 minutes to about 10 minutes, preferably about 5 minutes.

The compound of formula (XII) may be isolated, or may be carried on to the next step without isolation. Preferably the compound of formula (XII) is isolated.

Compounds of formula (XI) and (XIII) are commercially available.

Alternatively, a compound of formula (Xb), wherein $R^1$ is preferably para-nitrobenzyl;

and $R^2$ is preferably $C_{6-10}arylC_{1-6}alkyl$, such as benzyl; can be prepared by reacting a compound of formula (Xc), wherein $R^1$ is preferably para-nitrobenzyl; $R^2$ is preferably $C_{6-10}arylC_{1-6}alkyl$, such as benzyl; $R^3$ is preferably $C_{1-6}alkyl$, such as methyl; and $R^4$ is preferably $C_{1-6}alkyl$, such as methyl; with an oxidizing agent, in a solvent. Suitable oxidizing agents include ozone. Suitable solvents include methylene chloride, tetrahydrofuran or mixtures thereof, preferably methylene chloride. The aforesaid process is conducted at a temperature of about −70° C. The aforesaid process is conducted for a period of from about 1 hour to about 24 hours.

A compound of formula (Xc) is commercially available.

Alternatively, a compound of formula (Xb), wherein $R^1$ is preferably para-nitrobenzyl, and $R^2$ is preferably $C_{6-10}arylC_{1-6}alkyl$, such as benzyl; can be prepared by reacting a compound of formula (XV), wherein $R^2$ is preferably $C_{6-10}arylC_{1-6}alkyl$, such as benzyl; with a compound of formula (XVI)

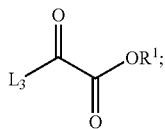

(XVI)

wherein $R^1$ is preferably para-nitrobenzyl, and $L_3$ is a leaving group, such as halo, preferably chloro, in a solvent in the presence of a base. Suitable solvents include methylene chloride, tetrahydrofuran or mixtures thereof. Suitable bases include diisopropylamine, triethylamine, pyridine or 2,6-lutidine. The aforesaid process is conducted at a temperature of from about −40° C. to about 25° C. The aforesaid process is conducted for a period of about 5 minutes to 15 minutes.

Compounds of formula (XVI) are commercially available.

Compounds of this invention can be crystallized or recrystallized from solvents such as organic solvents. In such cases solvates can be formed. This invention includes within its scope stoichiometric solvates including hydrates as well as compounds containing variable amounts of water that can be produced by processes such as lyophilization.

The compounds of formula (I) are useful for the preparation of a 3-cyclic-ether-substituted cephalosporin, i.e., the active compound. The active compound possesses activities against gram positive and gram negative bacteria. Methods for assaying the activity and methods for formulating and administering the active compounds are disclosed in U.S. Pat. No. 6,020,329, issued Feb. 1, 2000. Methods of treatments are also described in the aforesaid patent.

The following Examples illustrate the preparation of the compounds of the present invention. Melting points are uncorrected. NMR data are reported in parts per million (ppm) and are referenced to the deuterium lock signal from the sample solvent (deuteriochloroform unless otherwise specified). Commercial reagents were utilized without further purification. Room or ambient temperature refers to 20° C. to 25° C. All non-aqueous reactions were run under a nitrogen atmosphere for convenience and to maximize yields. Concentration at reduced pressure means that a rotary evaporator was used. TLC stands for thin liquid chromatography. HPLC stands for high pressure liquid chromatography. GC stands for gas chromatography.

EXAMPLE 1

Method A: from 7-AMINO-8-OXO-3-(TETRAHYDRO-FURAN-2-YL)-5-THIA-1-AZA-BICYCLO[4.2.0]OCTA-1 (6),2,4-TRIENE-2-CARBOXYLIC ACID 7-Amino-8-oxo-3-(tetrahydrofuran-2-yl)-5-thia-1-aza-bicyclo[4.2.0]octa-1(6),2,4-triene-2-carboxylic acid (20 g, 75 mmol), water (300 ml), acetone (400 ml), and a mixture of (Z)-2-amino-α-(methoxyimino)-4-thiazoleacetic acid anhydride and O,O-diethyl hydrogenphosphorothioate (27 g, 1.06 equivalents) were combined to form a slurry. The pH of the slurry was adjusted to between 7 to 7.5 by using aqueous sodium hydroxide. After complete dissolution was obtained, the reaction mixture was stirred for 3 hours. The product was precipitated by the addition of acetone (3200 mL). The resulting slurry was granulated, filtered, and dried under vacuo to give the title compound (29.0 g, 80%).

Method B: from ALLYL-7-(2-(2-AMINOTHIAZOL4-YL)-2-METHOXYIMINO)-3-TETRAHYDROFURAN-2-YL)-8-OXO-5-THIA-1-AZA-BICYCLO[4.2.0]OCT-2-ENE-2-CARBOXYLATE, BENZENE SULPHINIC ACID SALT To a 10-liter glass vessel was charged methylene chloride (4.50 liters) followed by tetrakis (triphenylphosphine) palladium (9.0 g, 7.8 mmoles) in nitrogen atmosphere. Triphenylphospbine (1.0 g, 3.8 mmoles) was added and stirred into the solution. Allyl-7-(2-(2-aminothiazol-4-yl)-2-methoxyimino)-3-tetrahydrofuran-2-yl)-8-oxo-5-thia-1-aza-bicyclo[4.2.0]oct-2-ene-2-carboxylate, benzene sulphinic acid salt (225.0g, 354 mmoles) was charged and warmed to 27–30° C. The reaction was monitored by HPLC, and further additions of catalyst was made as required. On completion, the solid product was filtered and washed twice with methylene chloride (700 ml total). The yellow to tan product was then air dried to achieve a constant weight before storage in a freezer.

EXAMPLE 2

| 7-Amino-8-oxo-3-(tetrahydrofuran-2-yl)-5-thia-1-aza-bicyclo[4.2.0]octa-1(6),2,4-triene-2-carboxylic acid | | |
|---|---|---|
| No. | Structure | Molecular Weight |
| 2 | (structure II) | 270.29 |

| Sodium 7-(2-(2-aminothiazol-4-yl)-2-methoxyimino)-3-(tetrahydrofuran-2-yl)-8-oxo-5-thia-1-aza-bicyclo[4.2.0]oct-2-ene-2-carboxylate | | |
|---|---|---|
| No. | Structure | Molecular Weight |
| 1 | (structure) | 453.48 |

7-Amino-8-oxo-3-(tetrahydrofuran-2-yl)-5-thia-1-aza-bicyclo[4.2.0]oct-2-ene-2-carboxylic acid 4-nitro-benzyl ester (20 g, 54 mmol), water (30 ml) and acetone (90 ml) were combined to form a slurry. The pH of the slurry was adjusted to 7 by using aqueous ammonia solution (15%). To the resulting solution was added sodium hydrosulfite (32 g, 3.8 equiv.) in water (40 mL) solution. The pH of the resulting solution was adjusted to 7 by using aqueous ammonia (15%) while maintaining the temperature between 40° C. to 45° C. After stirring for 1 hour at 45° C., the pH was re-adjusted to 3.5 with a hydrochloric acid aqueous solution (15%). The resulting slurry was granulated, filtered and dried to afford the title compound (11.3 g, 80%).

Preparation 1: (3-Benzyl-7-oxo-4-thia-2,6-diaza-bicyclo[3.2.0]hept-2-en-6-yl)-hydroxy-acetic acid-4-nitro-benzyl ester Isopropanol (500 mL), methylene chloride (1800 mL) and (1R)-(4-nitrophenyl)methyl ester-α,1-methylethylidene)-7-oxo-3-(phenylmethyl)-4-thia-2,6-diazabicyclo[3.2.0]hept-2-ene-6-acetic acid (250 g) were combined and the reaction mixture cooled at −70° C. To the cooled reaction mixture, ozone was bubbled until the ozonolysis was completed. To the resulting solution, a mixture of glacial acetic acid (625 mL) and isopropanol (750 mL) was added followed by a mixture of isopropanol (100 mL), water (100 mL) and sodium borohydride (22 g). After the reduction was completed, a sodium metabisulfite in water solution was added followed by the pH adjustment to 1.5 to 2.5 with hydrochloric acid (15%). The layers were separated and the organic layer was washed twice with aqueous sodium chloride (1000 mL). The organic layer was concentrated under vacuum and the resulting slurry granulated, filtered, and the cake washed with isopropanol. The product was dried under vacuo.

Preparation 2: Hydroxy-{2-oxo-4-[2-oxo-2-(tetrahydrofuran-2-yl)-ethylsulfanyl]-3-phenylacetylamino-azetidin-1-yl}-acetic acid 4-nitro-benzyl ester Bromine (51 g) and methanol (270 mL) were combined followed by a dropwise addition of a 1-(tetrahydro-2-furanyl)-ethanone (30 g) in methanol (30 mL) solution at 30° C. An aqueous sodium thiosulfate solution was then added followed by methylene chloride (300 mL). The layers were separated and the organic layer washed twice with an aqueous solution of sodium bicarbonate (300 mL). The resulting organic layer was concentrated followed by the addition of acetone (600 mL) and para-toluene sulfonic acid (6 g). After heating to reflux for 2 hours, the reaction was cooled and (3-benzyl-7-oxo-4-thia-2,6-diaza-bicyclo[3.2.0]hept-2-en-6-yl)-hydroxy-acetic acid 4-nitro-benzyl ester (100 g) and an additional para-toluene sulfonic acid (6 g) were charged. The resulting solution was stirred for 2 hours followed by a pH adjustment between 3 to 4 by using pyridine. The reaction was concentrated followed by the addition of water (180 mL), methylene chloride (600 mL) and hydrochloric acid (9 mL, 15%) to adjust the pH between 1 and 2. The layers were separated and the methylene chloride displaced with methanol (600 mL). Isopropanol (300 mL) was added to complete the precipitation and the resulting slurry was granulated, filtered and the cake washed with isopropanol. The product was dried under vacuo.

Preparation 3: 7-Amino-8-oxo-3-(tetrahydrofuran-2-yl)5-thia-1-aza-bicyclo[4.2.0]oct-2-ene-2-carboxylic acid 4-nitro-benzyl ester Thionyl chloride (45 ml, 0.615 mol) was added dropwise to a solution of hydroxy-{2-oxo-4-[2-oxo-2-(tetrahydrofuran-2-yl)-ethylsulfanyl]-3-phenylacetylamino-azetidin-1-yl}-acetic acid 4-nitro-benzyl ester (202 g, 0.362 mol) and 2,6-lutidine (58 ml, 0.500 mol) in dichloromethane (4 liters) at −20° C. After stirring for 1 hour, the solution was washed twice with saturated sodium chloride (1 liter) and concentrated. To the concentrated solution was added trimethylphosphine in tetrahydrofuran solution (110 ml, 3M, 330 mmol), the solution stirred for 1 hour, washed with diluted sodium hydrogen carbonate and saturated sodium chloride. After stirring at reflux for 16 hours, the solution was washed with water and saturated sodium chloride. The solution was concentrated and cooled to −40° C. followed by a dropwise addition of phosphorus pentachloride (104 g, 0.5 mol). α-Picoline (92 ml) in dichloromethane (60 ml) solution was added while maintaining the temperature between −40° C. to 30° C. The mixture was stirred for 1 hour followed by the addition of isopropanol (660 ml). The reaction mixture was warmed to 22° C., granulated, filtered and dried to give the title compound (250 g, 45%).

EXAMPLE 3

Allyl-7-(2-(2-Aminothiazol-4-yl)-2-methoxyimino)-3-tetrahydrofuran-2-yl)-8-oxo-5-thia-1-aza-bicyclo[4.2.0]oct-2-ene-2-carboxylate, benzene sulphinic acid salt

| No. | Structure | Molecular Weight |
|---|---|---|
| 3 | 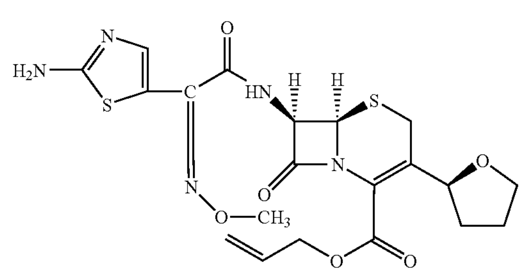 | 493.56 (634.62 as benzene sulphinic acid salt) |

Preparation 1: Allyl-7-phenylacetamido-3-(tetrahydrofuran-2-yl)-8-oxo-5-thia-1-aza-bicyclo[4.2.0]-oct-2-ene-2-carboxylate To a 100-liter glass vessel was added toluene (47 liters) and allyl-2-tri-n-methylphosphororanylidene-2-(3-phenylacetamido-4-(tetrahydrofuran -2-ylcarbonyl-methylthio) azetidin-on-1yl)acetate (1990 g). The solution was purged with nitrogen and brought to reflux. Any water present was collected and the solution was refluxed for 20 hours. After sampling for TLC/HPLC analysis, the solution was cooled back to ambient temperature. The solution was then run through Silica Gel 60 (4.5 kg), with the silica being further eluted with additional toluene (33 liters). The toluene was then stripped under vacuo at a maximum temperature of 60° C. Ethyl acetate was then added and was then stripped under vacuo at a maximum temperature of 60° C. To the semi solid oil was added tert-butyl methyl ether (2.5 liters) and the solution stirred overnight. The crystalline product was filtered off and washed with further tert-butyl methyl ether (0.3 liters). The mother liquors were concentrated and resubjected to silica chromatography (dissolved in 5 liters of toluene, added onto silica, eluted with 15 liters of toluene) and crystallized in the same fashion to afford a second crop. The product was isolated as a white crystalline solid. Yields range from 70% to 80%.

Preparation 2: Allyl-2-tri-n-methylphosphoranylidene-2-(3-phenylacetamido-4-(tetrahydrofuran-2-ylcarbonyl-methylthio)azetidin-on-1-yl)acetate The solution of allyl-2-hydroxy-2-(3-phenylacetamido-4-(tetrahydrofuran-2-ylcarbonyl-methylthio)azetidin-on-1-yl) acetate in tetrahydrofuran, which was obtained from Preparation 1 of Example 3, was further diluted with additional tetrahydrofuran (total tetrahydrofuran was 12 liters). The solution was cooled back to −20° C. under nitrogen and 2,6-lutidene (654.0 g, 6.09 moles) was added, followed by a dropwise addition of thionyl chloride (724.0 g, 6.09 moles) at a maximum temperature of −20° C. After a thirty minute stirring, the solution was allowed to warm to −10° C. and sampled for TLC. The TLC showed that the starting material was converted into allyl-2-chloro-3-(3-phenylacetamido-4-(tetrahydrofuran-2-ylcarbonyl -methylthio)azetidin-on-1-yl) acetate to completion. The precipitated compounds were then filtered off and washed further with tetrahydrofuran. The tetrahydrofuran solution was then concentrated under vacuo at a maximum temperature of 30° C., redissolved in fresh tetrahydrofuran (6 liters) and cooled back to −10° C. After stirring overnight at ambient temperature, the solution was sampled for completion, diluted with ethyl acetate (35 liters) and washed with 5% sodium bicarbonate (20 liters) and 20% saturated sodium chloride (20 liters). The ethyl acetate was then stripped under vacuo at a maximum temperature of 40° C. to afford thick dark oil. The yields range from 88% to 90%.

Preparation 3: Allyl-2-hydroxy-2-(3-phenylacetamido-4-(tetrahydrofuran-2-ylcarbonyl-methylthio)azetidin-on-1-yl) acetate To a 20-liter flask was added methylene chloride (10.0 liters), tetrahydrofuran (1.0 liter) and allyl 2-hydroxy-2-(3-benzyl4-thia-2,6-diazabicyclo[3.2.0]hept-2-en-7-one)acetate (2016 g, 6.05 moles). To this solution was added 45% aqueous para-toluene sulphonic acid solution (500.0 g). After a three hour stirring the solution was sampled for completion with TLC. The solution was then transferred to a 50 liter glass separating vessel, and methylene chloride was added (5 liters) followed by water (2 liters). The separated organic phase was then washed with water (4 liters). The methylene chloride phase was then dried over sodium sulphate to afford a dry solution of allyl-2-hydroxy-2-(3-phenylacetamido4-mercapto-azetidin-on-1-yl)acetate in methylene chloride that was then used without delay. To the above solution was added 86% of the solution of 2-bromoacetyltetrahydrofuran in methylene chloride (6.3 moles). The resultant solution was stripped under vacuo at a maximum temperature of 30° C. to 50% of its volume. Pyridine (503.1 g, 6.36 moles) was added at a maximum temperature of 10° C. The solution was stirred overnight, diluted with methylene chloride (10 liters) and washed twice with water (10 liters total) then once with saturated sodium chloride (10%, 10 liter). After drying over sodium sulphate, the solution was concentrated under vacuo at a maximum temperature of 40° C. to ensure dryness. The solution was redissolved in tetrahydrofuran (5 liter) for use in the next step. If storage was required, the tetrahydrofuran solution was stored and dried before use.

Preparation: 4: 2-Bromoacetyltetrahydrofuran

To a 20-liter glass vessel was added methylene chloride (10.0 liters) followed by acetyltetrahydrofuran (838.0 g, 7.34 moles). The solution was then cooled back to −10° C. and triethylamine was added (854.0 g, 8.44 moles). The vessel was purged with nitrogen and trimethylsilane triflate (1713.0 g, 7.71 moles) was added dropwise at a maximum temperature of −8° C. Addition was typically complete in 45 minutes. After 15 minutes stirring, a sample was removed for TLC and GC analysis, which showed that the reaction was completed. N-bromosuccinimide (1340 g. 7.53 moles) was added to the solution at a maximum temperature of −5° C. over a period of approximately 45 minutes in six portions. After a 30 minute stirring, the solution was sampled for GC and TLC analysis, which showed that the reaction was completed. The solution was then transferred to a 50-liter separating vessel, and 5% sodium bicarbonate (5 liters) was added with caution. The solution was stirred and separated. The upper aqueous phase was discarded, and the methylene chloride phase was washed with water, dried over sodium sulphate, filtered and stored in a freezer before use in the next step.

Preparation 5: Allyl-2-hydroxy-2-(3-benzyl-4-thia-2,6-diazabicyclo[3.2.0]hept-2-en-7-one)acetate.

To a 50-liter glass vessel was added methylene chloride (20.6 liters) followed by 3-benzyl4-thia-2,6-diazabicyclo [3.2.0]hept-2-en-7-one (1700 g, 7.79 moles). To this suspension was added allyl glyoxylate monohydrate (1285 g, 9.74 moles) followed by sufficient triethylamine (about 175 g) to bring the pH of the solution to 7.5–7.9. After a 1 hour stirring, the solution was sampled for TLC/HPLC analysis. Upon completion, the solution was quenched with 0.1 M of hydrochloric acid (2.75 liters) to a pH of 4.50–5.00. The upper aqueous phase was discarded, and the methylene chloride phase was washed with water (8 liters) and saturated sodium chloride (8 liters). The solution was dried over sodium sulphate and concentrated to a thick oil. The oil was dispersed in hexane (5 liters), filtered, and reslurried in tert-butyl methyl ether (5 liters) before filtration and washing with further tert-butyl methyl ether. Air drying afforded an off white crystalline product. Yields range from 72–99%.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

The invention claimed is:

1. A process for preparing a 3-cyclic-ether substituted cephalosporin of the formula I:

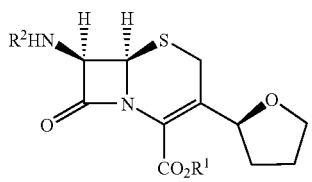

or a pharmaceutically acceptable salt thereof, wherein the group $CO_2R^1$ is a carboxylic acid or a carboxylate salt; and $R^2$ has the formula

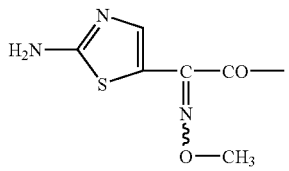

comprising reacting a compound of formula II

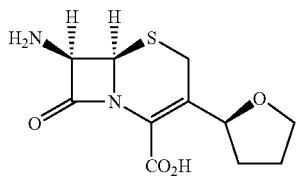

with a compound of the formula III $$R^2L \qquad III$$

wherein $R^2$ is as defined above; and
L is di-($C_{1-6}$ alkyl)phosphorothioate; in the presence of a solvent and a base.

2. The process according to claim 1 further comprising the step of preparing said compound of formula II by reacting a compound of formula IV:

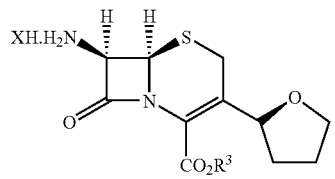

wherein $R^3$ is para-nitrobenzyl or allyl; and X is halo;
with a suitable deprotecting agent; in the presence of a solvent.

3. A process according to claim 1, wherein L of said compound of the formula III is diethylphosphorothioate.

4. A process according to claim 1, wherein said solvent is acetone.

5. A process according to claim 1 wherein said base is sodium hydroxide.

6. A process according to claim 2, wherein X is chloro.

7. A process according to claim 2, wherein said $R^3$ is para-nitrobenzyl and said suitable deprotecting agent is sodium dithionite or a catalytic hydrogenating agent.

8. A process according to claim 2, wherein said $R^3$ is allyl and said suitable deprotecting agent is tetrakis triphenylphosphine palladium (0).

9. A process according to claim 7, wherein said solvent is acetone, water, tetrahydrofuran or mixtures thereof.

10. A compound of formula II:

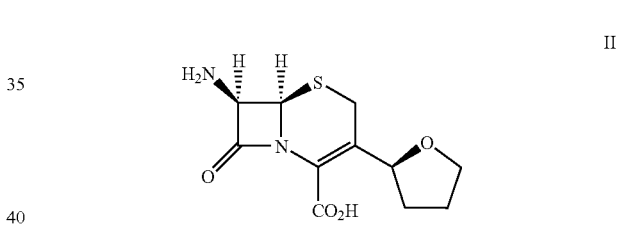

11. The compound according to claim 10 wherein said compound of the formula II has an enantiomeric or diasteriomeric purity of 96% to 100%.

12. A process according to claim 2 wherein $R^3$ is para-nitrobenzyl.

* * * * *